US00PP37485P2

(12) United States Plant Patent
Smit

(10) Patent No.: US PP37,485 P2
(45) Date of Patent: Jun. 23, 2026

(54) ***BEGONIA* PLANT NAMED 'EC-BEGO-2503'**

(50) Latin Name: *Begonia kingiana*
Varietal Denomination: EC-BEGO-2503

(71) Applicant: Eden Collection B.V., Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 19/235,286

(22) Filed: Jun. 11, 2025

(51) Int. Cl.
*A01H 5/12* (2018.01)
*A01H 6/18* (2018.01)

(52) U.S. Cl.
USPC ..... Plt./343

(58) Field of Classification Search
USPC ..... Plt./343

CPC ... A01H 5/12; A01H 5/02; A01H 5/00; A01H 6/185; A01H 6/18
See application file for complete search history.

(56) References Cited

PUBLICATIONS

Community Plant Variety Office (CPVO) Application Consultation Version 4.23.11, retrieved on Sep. 9, 2025 at https://online.plantvarieties.eu/publicConsultation Details?registerId=20250622&denomination=ec%20bego%202503, 2 pp. (Year: 2025).*

* cited by examiner

*Primary Examiner* — June Hwu

(57) ABSTRACT

A new and distinct cultivar of *Begonia* plant named 'EC-BEGO-2503' is disclosed, characterized by glossy leaves with a unique pattern created by lighter colored veins. Foliage has a distinct bright yellow-green coloration surrounding venation on both upper and lower surfaces. Plants have compact habits, and flower from spring to autumn. The new cultivar is a *Begonia*, typically used as an ornamental plant.

3 Drawing Sheets

Latin name of the genus and species: *Begonia kingiana*.
Cultivar denomination: 'EC-BEGO-2503'.

BACKGROUND OF THE INVENTION

The new cultivar is a product of a planned breeding program to produce distinct and better performing *Begonia* cultivars. The new cultivar was selected as a seedling resulting from the crossing made by the inventor, Obed J. Smit, a citizen of the Netherlands, in 2021. The seed parent is *Begonia kingiana*, the specie itself, origin A. The pollen parent *Begonia kingiana*, the specie itself, origin B. The new cultivar was selected by the inventor in 2023 at a commercial greenhouse in Sappemeer, the Netherlands.

Asexual reproduction of the new cultivar 'EC-BEGO-2503' by terminal cuttings was first performed in Sappemeer, the Netherlands at a commercial greenhouse in March 2023, and has shown that the unique features of this cultivar are stable and reproduced true to type through successive generations.

SUMMARY OF THE INVENTION

The cultivar 'EC-BEGO-2503' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-2503'. These characteristics in combination distinguish 'EC-BEGO-2503' as a new and distinct *Begonia* cultivar:

1. Glossy leaves with a unique pattern created by lighter colored veins.
2. Distinct bright yellow-green coloration surrounds venation on both upper and lower surfaces.
3. Compact plant habit.

PARENT COMPARISONS

Plants of the new cultivar 'EC-BEGO-2503' are similar to plants of the female parent in most horticultural characteristics, however, plants of the new cultivar 'EC-BEGO-2503' differ in the following characteristics:

1. Leaves of the new cultivar are about 30% smaller than leaves of the seed parent.
2. Leaf stems of the new cultivar are short, making a more compact plant. Leaf stems of the seed parent are long, making a more open and larger plant.
3. Leaf pattern of the new cultivar is darker colored than the leaf pattern of the seed parent.

Plants of the new cultivar 'EC-BEGO-2503' are similar to plants of the male parent in most horticultural characteristics, however, plants of the new cultivar 'EC-BEGO-2503' differ in the following characteristics:

1. Leaves of the new cultivar are about 20% larger than leaves of the pollen parent.
2. Plants of the new cultivar are not as compact as plants of the pollen parent.
3. Leaf pattern of the new cultivar is not as dark as the leaf pattern of the pollen parent.

COMMERCIAL COMPARISONS

Plants of the new cultivar 'EC-BEGO-2503' are similar to plants of the commercial cultivar *Begonia cleopatrae*, the species itself, unpatented. However, plants of the new cultivar differ in the following characteristics:

1. Leaves of the new cultivar are glossy with a unique leaf pattern created by the lighter colored veins. Leaves of this comparator are dull grey-green with a light green main vein and light green spots at the leaf rim.
2. Plants of the new cultivar are not as compact as plants of this comparator.

Plants of the new cultivar 'EC-BEGO-2503' are similar to plants of the commercial cultivar *Begonia rex* 'Rondeau', unpatented. However, plants of the new cultivar differ in the following characteristics:

1. Leaves of the new cultivar are glossy with a unique leaf pattern created by the lighter colored veins. Leaves of this comparator are dull red-brown with light green spots, not located at the 6 veins but scattered around the leaves.
2. Plants of the new cultivar are more compact than plants of this comparator.

BRIEF DESCRIPTION OF THE PHOTOGRAPHS

The accompanying photograph in FIG. 1 illustrates in full color a typical blooming plant of 'EC-BEGO-2503' grown in a greenhouse. The plant is approximately 30 weeks of age.

Figure 1:
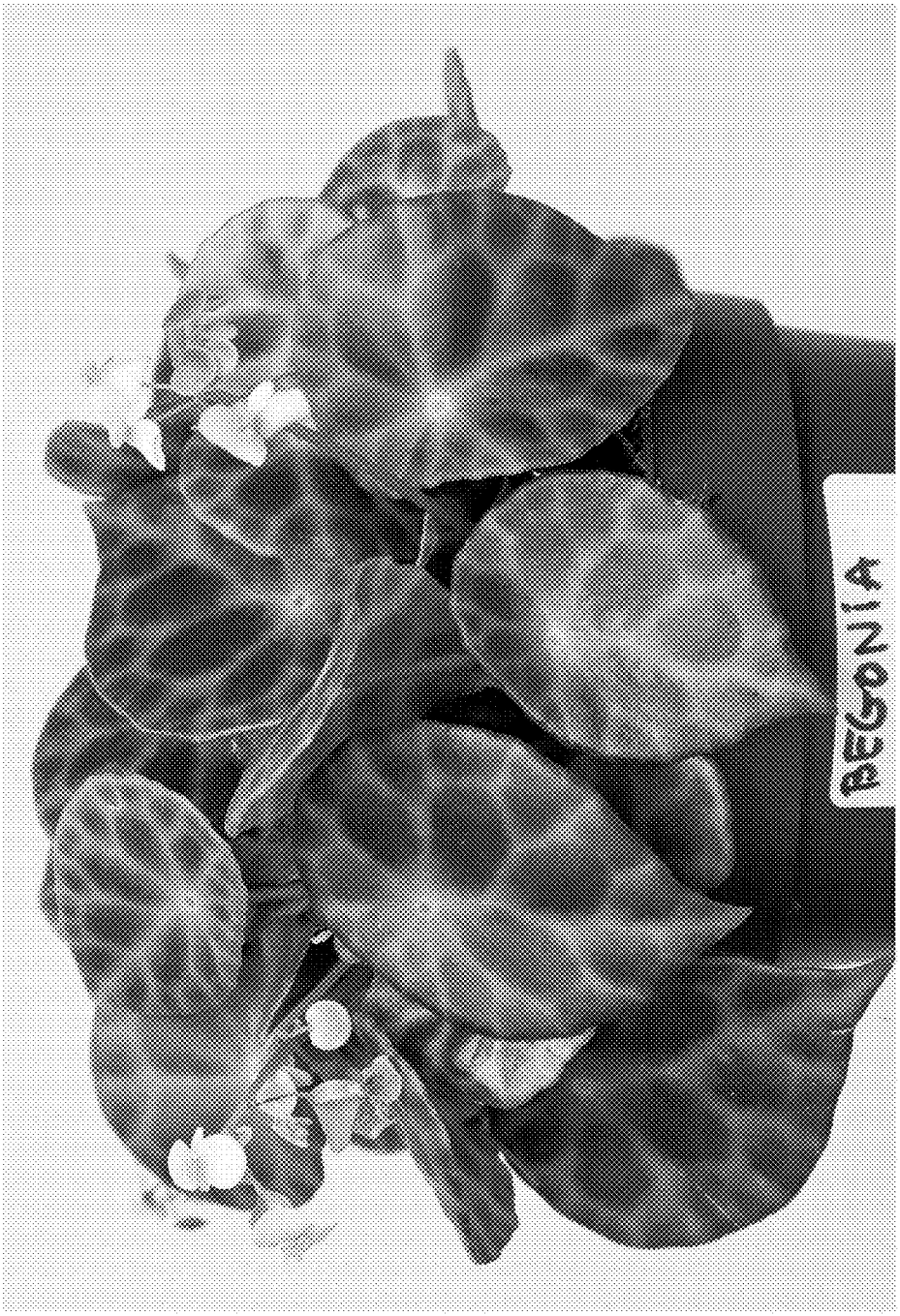
Figure 2:
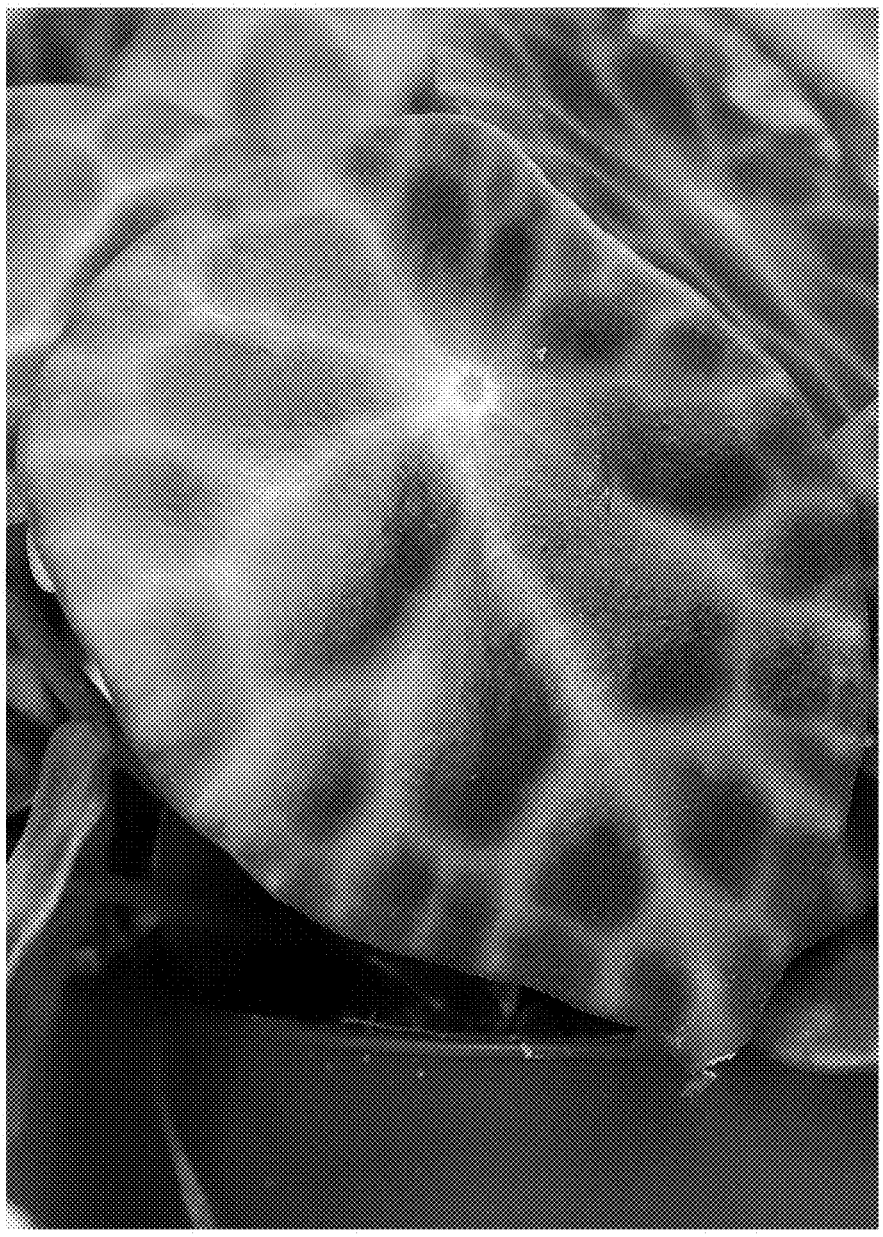
FIG. 2 illustrates a close up of the foliage.
Figure 3:
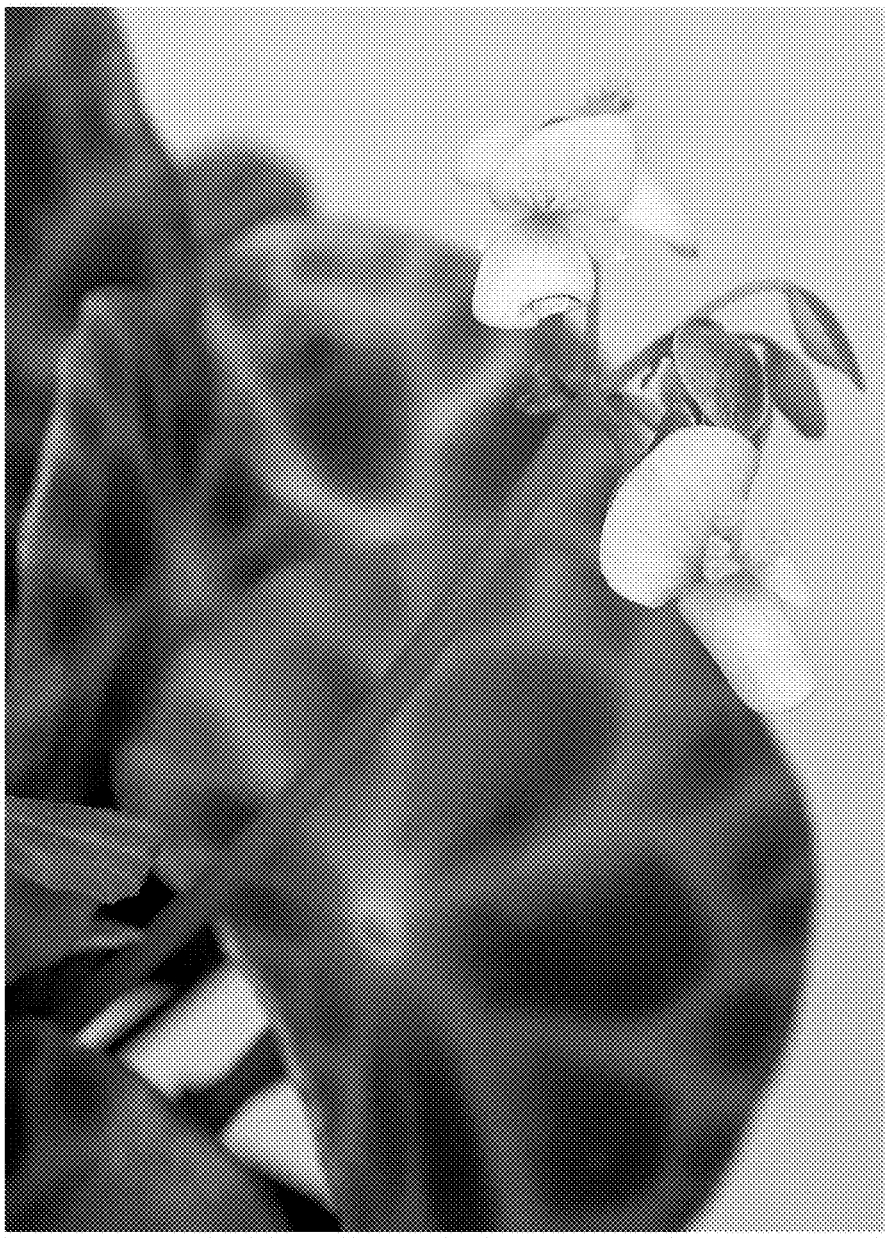
FIG. 3 shows foliage and flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 (reprint) except where general terms of ordinary dictionary significance are used. The following observations and measurements describe 'EC-BEGO-2503' plants at 30 weeks of age, grown in April in a greenhouse in Sappemeer, the Netherlands. The growing temperature ranged from 17° C. to 18° C. at night to 19° C. to 21° C. during the day. Measurements and numerical values represent averages of typical flowering types.

Botanical classification: *Begonia kingiana* 'EC-BEGO-2503'.

PROPAGATION

Time to initiate roots: About 21 days at approximately 21° C. in summer.

Time to produce rooted cutting: About 100 days at 21° C. in summer.

Description of roots: Herbaceous, fine, moderately dense, freely branching. Brown in color, not accurately measured with R.H.S. chart.

PLANT

Plant type: Perennial potted plant.

Plant shape: Broad dome.

Growth habit: Broad, spreading, upright.

Plant spread: Average 9.5 cm.

Height: Average 8.5 cm to top of foliar plane; 18 cm to top of floral plane.

Growth rate: Moderate.

Plant vigor: Moderate.

Age of plant described: Approximately 30 weeks from tissue culture.

Branching habit: Leaves growing from basal clumps; no main branches and lateral branches present.

Pinching: Pinching not required.

Number of primary branches per plant: Average 9 basal clumps.

FOLIAGE

Leaf:

*Arrangement*.—Alternate, in basal clumps.

*Quantity*.—Average 12.

*Average length*.—7.6 cm.

*Average width*.—4.8 cm.

*Shape of blade*.—Obliquely ovate.

*Apex*.—Apiculate. Base: Rounded, peltate connection of petiole to lamina.

*Margin*.—Very shallow, bluntly and coarsely dentate.

*Texture of top surface*.—Glabrous, slightly velvety.

*Texture of bottom surface*.—Glabrous, velvety.

*Pubescence*.—None.

*Luster, upper side*.—Glossy.

*Luster, under side*.—Glossy.

*Rugosity, upper side*.—Non-rugose.

*Rugosity, under side*.—Non-rugose.

*Color*.—Young foliage upper side: RHS Greyed-Orange 175A and 175B, veined Yellow-Green 144B. Evenly rounded blotch at petiole attachment colored Greyed-Green 191A surrounded by a halo of Yellow-Green 150A. Young foliage under side: RHS Greyed-Orange 176B, veined Yellow-Green 145B. Mature foliage upper side: A blend of RHS Greyed-Green N189A and Black and 202A, areas adjacent to main veins and secondary veins Yellow-Green 143B. Evenly rounded blotch at petiole attachment colored Greyed-Green 191A surrounded by a halo of Green-White 157A. Mature foliage under side: A blend of RHS Greyed-Orange 176B and 177A, area adjacent to main veins and secondary veins Yellow-Green 145A.

*Venation*.—Pattern: Rotate. Venation color upper side: RHS Yellow-Green 147A. Venation color under side: RHS Yellow-Green N148A and N148B.

*Petiole*.—Length: Average 6.9 cm. Diameter: Average at proximal end: 0.3 cm, average at distal end: 0.2 cm. Texture: Glabrous, smooth. Luster: Slightly glossy. Strength: Low. Color, upper side: RHS Greyed-Orange 176A, moderately covered with small lenticels, average length: 0.15 cm, average diameter: 0.3 mm, colored Greyed-Green 196C. Color, under side: RHS Greyed-Orange 174B, moderately covered with small lenticels, average length: 0.15 cm, average diameter: 0.3 mm, colored Greyed-Green 196C.

*Stipules*.—Quantity: 1 stipule present at the base. Shape: Ovate to near deltoid. Average Length: 1.5 cm. Average width: 0.8 cm. Apex: Narrow apiculate. Base: Broad cuneate. Margin: Entire. Color: Both sides colored a transparent blend of RHS Greyed- Orange 164D and N170D, main vein colored Greyed-Orange 165B to 165D.

FLOWER

Inflorescence:
*Type and form*.—Panicle.
*Height*.—Average: 9.6 cm (including peduncle).
*Diameter*.—Average: 4.3 cm.
*Quantity of flowers per inflorescence*.—Average 12 in an average of 9 male flowers and 3 female flowers.
*Quantity of flowers per plant*.—Average 7 in an average of 4 male flowers and 3 female flowers.
*Quantity of flower buds per plant*.—Average 89.
*Quantity of flowers and buds per plant*.—Average 96.
*Natural flowering season*.—Spring to autumn.

Flower bud:
*Length*.—Male and female buds 0.7 cm; immature ovary in females 0.5 cm.
*Diameter*.—Male and female buds 0.7 cm; immature ovary in females 0.6 cm.
*Shape*.—Orbicular, flattened.
*Texture*.—Glabrous, smooth.
*Luster*.—Moderately glossy.
*Color*.—Male and female buds RHS Greyed-Orange 169A, 169B and 169C.

Flower:
*Type and form*.—Male flowers and female flowers rotate, single.
*Aspect*.—Upright to outwardly.
*Fragrance*.—None.
*Shape*.—Rotate, single.
*Height*.—Male flowers average: 1.9 cm. Female flowers average: 1.7 cm.
*Diameter*.—Male flowers average: 0.9 cm. Female flowers average: 1 cm.
*Length*.—Male flowers average: 0.8 cm. Female flowers average: 1.5 cm.
*Longevity on plant*.—Average 1 week.
*Persistence*.—Self-cleaning.

Tepals:
*Arrangement*.—Rotate.
*Quantity per flower*.—Male flowers average: 4. Female flowers average: 3.
*Number of whorls*.—Male flowers average: 1. Female flowers average: 1.
*Shape*.—Male, large tepals: Broad ovate to near orbicular. Female, large tepals: Broad ovate to near orbicular. Male, small tepals: Narrow elliptic. Female, small tepals: Oblanceolate.
*Length*.—Male, large tepals: 1 cm. Female, large tepals: 0.8 cm Male, small tepals: 0.5 cm. Female, small tepals: 0.5 cm.
*Width*.—Male, large tepals: 0.9 cm. Female, large tepals: 1 cm. Male, small tepals: 0.15 cm. Female, small tepals: 0.25 cm.
*Apex*.—Male, large tepals: Obtuse. Female, large tepals: Obtuse. Male, small tepals: Bluntly acute. Female, small tepals: Bluntly acute.
*Base*.—Male, large tepals: Cuneate. Female, large tepals: Cuneate. Male, small tepals: Bluntly acute. Female, small tepals: Bluntly acute.
*Margin*.—Entire, all tepals.
*Texture*.—Lower: Smooth, glabrous, velvety. Upper: Smooth, glabrous, moderately velvety.
*Rugosity*.—Non-rugose.
*Luster*.—Lower: Very slightly glossy. Upper: Slightly glossy.
*Color*.—When opening: Large, upper side: Male and female RHS Green-White 157D, slightly to very strongly tinged Red 49D. Small, upper side: Male and female RHS White 155C. Large, under side: Male and female RHS Green-White 157D, slightly to very strongly tinged Orange-Red 35B to 35D. Small, under side: Male and female RHS White 155C. Fully opened: Large, upper side: Male and female RHS Green-White 157D, slightly to very strongly tinged Red 49D. Small, upper side: Male and female RHS White 155C. Large, under side: Male and female RHS Green-White 157D, slightly to very strongly tinged Orange-Red 35B to 35D. Small, under side: Male and female RHS White 155C.

Peduncle:
*Terminal length*.—Average 8 cm.
*Terminal diameter*.—Average at proximal end: 0.2 cm, average at distal end: 0.15 cm.
*Angle to lateral branch axis*.—Average 50°.
*Strength*.—Weak.
*Texture*.—Glabrous, smooth.
*Luster*.—Moderately glossy.
*Color*.—RHS Greyed-Red 179A, fading to Greyed-Orange 164A towards the distal end.

Pedicel:
*Length*.—Average 1 cm.
*Diameter*.—Male: Average 0.75 mm. Female: Average 1 mm.
*Angle to lateral branch axis*.—Average 45° to peduncle.
*Strength*.—Weak.
*Texture*.—Glabrous, smooth.
*Luster*.—Moderately glossy.
*Color*.—Male: RHS Greyed-Yellow 160B. Female: RHS Greyed-Orange 173B.

REPRODUCTIVE ORGANS

Stamens:
*Number*.—Average 45 per flower.
*Filament length*.—Average 0.75 mm.
*Filament color*.—RHS Yellow 13B.
*Anther shape*.—Oblong, slightly curved.
*Anther length*.—Average 0.1 cm.
*Anther width*.—Average 0.5 mm.
*Anther color*.—RHS Yellow 10A.
*Pollen*.—None.

Pistil:
*Number*.—Average 3 per flower.
*Length*.—Average 0.5 cm.
*Stigma diameter*.—Average 0.2 cm.
*Stigma shape*.—Spiral, cleft in two fringed stigmas.
*Stigma color*.—RHS Yellow 12A.
*Style length*.—Average 0.35 cm.
*Style color*.—RHS Yellow-Green N144B.
*Ovary color*.—RHS Yellow-Green 145A.

OTHER CHARACTERISTICS

Seeds and fruits: None observed to date.

Disease/pest resistance: Similar resistance nor susceptibility to normal diseases and pests of *Begonia* has been observed.

Temperature tolerance: Tolerates temperatures up to 35° C. Hardy to USDA zones 10 to 12. Low to moderate tolerance to rain. Low tolerance to wind.

What is claimed is:

1. A new and distinct cultivar of *Begonia* plant named 'EC-BEGO-2503' as herein illustrated and described.

* * * * *